United States Patent [19]

Lazzeri et al.

[11] Patent Number: 5,191,115
[45] Date of Patent: Mar. 2, 1993

[54] METHOD FOR OBTAINING CARBOXYLIC ACIDS BY REACTION OF ALKANES AND FORMIATES

[75] Inventors: Véronique Lazzeri, Marseille; Roger Gallo, Bouc Bel Air; Rachid Jalal, Marseille, all of France

[73] Assignee: Atochem, Paris, France

[21] Appl. No.: 623,715

[22] PCT Filed: Apr. 5, 1990

[86] PCT No.: PCT/FR90/00243
§ 371 Date: Feb. 5, 1991
§ 102(e) Date: Feb. 5, 1991

[87] PCT Pub. No.: WO90/12779
PCT Pub. Date: Nov. 1, 1990

[30] Foreign Application Priority Data

Apr. 18, 1989 [FR] France .................. 89 05153

[51] Int. Cl.$^5$ .............................. C07C 61/12
[52] U.S. Cl. .................... 562/499; 562/400; 562/501; 562/504; 562/601
[58] Field of Search ............... 562/497, 521, 400, 499, 562/501, 504, 606

[56] References Cited

U.S. PATENT DOCUMENTS 4,002,674 1/1977 Inamoto .............................. 562/499

Primary Examiner—Michael L. Shippen
Attorney, Agent, or Firm—Burns, Doane, Swecker & Mathis

[57] ABSTRACT

To produce a carboxylic acid $R^1$—COOH, in which $R^1$ is a tertiary branched alkyl residue or a cycloalkyl residue with one or more rings, which may be attached, and possibly substituted by at least one alkyl residue, the alpha carbon atom of the carbonyl group being a tertiary carbon atom, a branched or cyclic alkane $R^1H$, in which $R^1$ is a branched alkyl residue or a cycloalkyl residue with one or more rings, which may be attached, and possibly substituted by at least one alkyl residue, the alpha carbon atom of the hydrogen atom being a tertiary carbon atom or a secondary carbon atom capable of being rearranged during reaction to a tertiary atom, is reacted in the presence of an acid catalyst with a formiate $H(CO)O(CR^2R^3R^4)$, in which $R^2$, $R^3$ and $R^4$ denote hydrogen or alkyl, under the three following conditions: that $R^2$, $R^3$ and $R^4$ are not simultaneously hydrogen; that the formiate yields, in the reaction medium, directly or following a rearrangement, a stable $R^2R^3R^4C^+$ cation; and that the alkane $R^2R^3R^4CH$ formed can be easily eliminated from the reaction medium.

13 Claims, No Drawings

METHOD FOR OBTAINING CARBOXYLIC ACIDS BY REACTION OF ALKANES AND FORMIATES

The present invention concerns a process for the preparation of carboxylic acids wherein the carbon atom in alpha of the carboxylic group is a tertiary carbon atom, the process consisting of reaction the corresponding alkanes with formiates.

The Koch synthesis of branched carboxylic acids is carried out by the reaction of olefins with carbon monoxide and water, catalyzed by inorganic acids, such as sulfuric acid or phosphoric acid, at moderate temperatures and pressures:

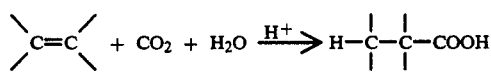

wherein:

generally represents isobutene or an olefin with $C_5$–$C_{10}$.

The reaction of Koch and Haaf is a variant at atmospheric pressure of the Koch reaction wherein carbon monoxide is introduced by the decomposition of formic acid and wherein the derivative to be carbonylated may be an olefin or an equivalent functional derivative (F. Falbe, "New syntheses with carbon monoxide", Springer, Weinheim, 1980):

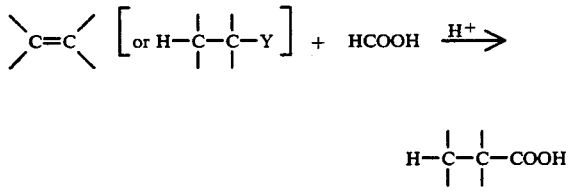

wherein:

generally represents isobutene or an olefin with $C_5$–$C_{10}$.
Y is a hydroxyl, halogen or alkoxyl radical.

Another method of the direct synthesis of carboxylic esters is also known by the reaction of an olefin and an alkyl formiate in the presence of an inorganic acid, such as sulfuric acid (EP-A-0 219 948; EP-A-0 092 350; EP-A-0 106 656):

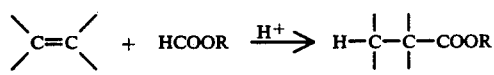

wherein:

generally represents isobutene or an olefin with $C_5$–$C_{10}$.
R preferably is a methyl group or a primary alkyl group with $C_2$–$C_{10}$.

It is equally possible, according to the work of Haaf and Koch, to prepare at atmospheric pressure carboxylic acids from alkanes, by using formic acid as the source of carbon monoxide and a functional derivative RY, which serves to activate the alkane to be carbonylated:

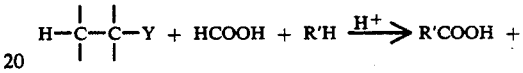

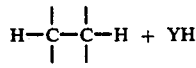

wherein:
R' represents an isoalkane and
Y is as defined above.

The applicant has now discovered that it is possible to obtain carboxylic acids of the type indicated above by the direct reaction of an alkane with a formiate, without it being necessary to add formic acid to the reaction medium.

The advantage of the process according to the invention is that it makes it possible to obtain carboxylic acids of the aforementioned type by carboxylation at the ambient temperature and pressure. Furthermore, this reaction may be carried out by means of alkanes or alkane fractions, the chemical conversion of which is difficult. Finally, an additional advantage of the process is due to the fact that it makes possible the use of formiates (which may be obtained industrially by capturing carbon monoxide in the gaseous effluents of certain industrial processes) serving as the liquid transport medium of carbon monoxide and as an alkane activator.

The first object of the present invention is thus a process for the preparation of a carboxylic acid represented by the Formula (I):

$$R^1\text{---COOH} \qquad (I)$$

wherein $R^1$ represents a tertiary branched alkyl radical or a cycloalkyl radical with one or several rings, attached or not, and optionally substituted by at least one alkyl radical, with the carbon in alpha of the carbonyl group being a tertiary carbon atom, characterized in that a branched or cyclic alkane of Formula (II):

$$R^1H \qquad (II)$$

in which $R^1$ is a branched alkyl radical or a cycloalkyl radical with one or several rings, attached or not, and optionally substituted by at least one alkyl radical, the carbon atom in alpha of the hydrogen atom being a tertiary atom or a secondary atom capable of being rearranged in the course of the reaction into a tertiary atom, with a formiate of Formula (III):

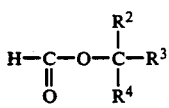

(III)

wherein $R^2$, $R^3$ and $R^4$ each independently represent a hydrogen atom or an alkyl radical, with the triple condition that $R^2$, $R^3$ and $R^4$ do not represent simultaneously a hydrogen atom, that the compound (III) lead in the reaction medium, directly, or after rearrangement, to a stable cation $R^2$, $R^3$, $R^4C^4$, and that the alkane formed from the cation may be readily eliminated from the reaction medium.

The reaction scheme is thus the following:

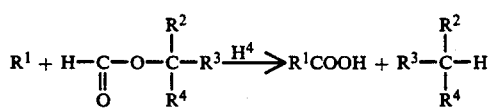

In this novel reaction the formiate of Formula (III) decomposes in the presence of an acid, to yield carbon monoxide and a cation $R^2R^3R^4C^4$.

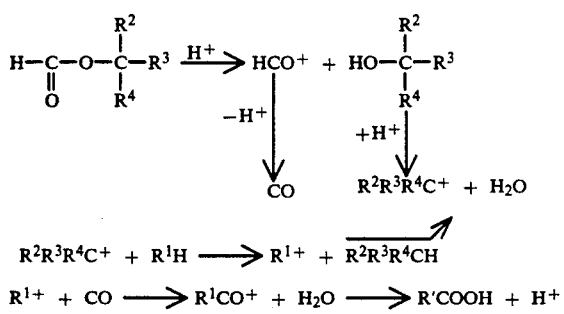

With respect to the carboxylation reactions of Haaf and Koch carried out with alkanes, it is no longer necessary to introduce a H—C—C—Y (RY) functional derivative to provide a stable tertiary cation required to transfer the hydride, nor formic acid to furnish carbon monoxide, due to the fact that the formiate of Formula (III) decomposes in situ to provide these two reagents. Furthermore, relative to the reactions described by Haaf, no water is released (which is the case if (RY=-ROH), which dilutes the reaction medium and reduces the activity of the mixture or an acid HX (if RY=an alkyl halide RX), which has a corrosive effect in the medium. In particular, carboxylic acids of Formula (Ia) are prepared

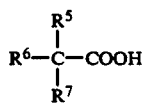

(Ia)

wherein:
$R^5$, $R^6$ and $R^7$ each independently represent an alkyl radical with $C_1$-$C_{10}$; or
two radicals $R^5$ to $R^7$ are combined to form a —(CH$_2$)$_n$—, n being an integer from 4 to 11 and the third represents an alkyl radical $C_1$-$C_7$; or
$R^5$, $R^6$ and $R^7$ are combined with each other and with the carbon atom carrying them, to form a cycloalkyl radicals with one, two or three rings.

As an alkane of Formula (II), the following may be cited as examples: isopentane, 2,3-dimethyl butane, 2-methyl pentane, 2-methyl hexane, methylcyclopentane, 1,4-dimethyl cyclohexane, decahydronaphthalene and adamantane.

In the process according to the invention, it is necessary to use a formiate that leads in the reaction medium to a stable $R^2R^3R^4C^+$ cation. This stable cation is obtained in particular in the case in which the carbon atom carrying the $R^2$, $R^3$ and $R^4$ radicals is a tertiary carbon atom (for example if tertisobutyl formiate is used) or if this carbon atom is a secondary carbon atom and the resultant cation rearranges into a secondary cation (for example, if isobutyl formiate is used, wherein the isobutyl cation is arranged into the tertisobutyl cation).

However, an additional condition is that the $R^2R^3R^4CH$ compound be easily eliminated from the medium, whereby the equilibrium is displaced in the sense of the formation of Compound (I). For this reason, cations for which $R^2$, $R^3$ and $R^4$ represent an aryl group are not suitable, together with those in which $R^2$, $R^3$ and $R^4$ each represents an alkyl radical having, for example, more than 6 carbon atoms.

The term "alkyl" in the definition of Formula (III) is intended to signify alkyl groups in $C_1$ to $C_6$, in particular lower alkyl groups in $C_1$ to $C_5$ and cycloalkyl groups in $C_5$, $C_6$.

Therefore, as the formiate of Formula (III) in particular tertiobutyl formiate or isobutyl formiate may be used, as both produce isobutane which is gaseous over the entire temperature range and is easily released from the reaction medium, thereby displacing the equilibrium toward the formation of carboxylic acid.

To catalyze the reaction, preferably at least one inorganic acid is used, which specifically may be sulfuric acid or phosphoric acid, or their mixture, the acid being used in the liquid state, with a concentration or strength of at least 80%, even up to 100%. Sulfuric acid is preferred in a strength of at least 95%.

The process of the preparation of a carboxylic acid according to the invention consists of adding the formiate (III) to a mixture of the alkane (II) and at least one acid as the catalyst, and vigorously agitating the reaction medium at the ambient temperature or at a temperature slightly higher. Vigorous agitation is generally desirable for the reaction, in view of the existence of two phases. The molar alkane (II)-formiate (III) ratio generally is between about 0.5 and 3. However, it is preferably to work with an excess in alkane, which improves the yield. The temperature of the reaction is not a critical parameter, it may be between about 0° C. and the reflux temperature of the alkane to be carbonylated, for example between 0° C. and about 80° C.; the reaction may be carried out in particular at the reflux temperature of the solvent, for example at about 65°-70° C. if CCl$_4$ is used as the solvent. However, there is no difficulty in carrying out the reaction at the ambient temperature.

The duration of the reaction again is not a critical parameter; reaction times generally extending from 1 to 5 h may be mentioned.

The process according to the present invention may be carried out in s solvent medium. A solvent of the carbon tetrachloride type is generally used, but it is not absolutely necessary, it may be replaced by an excess in the alkane. This result confirms that carbon tetrachloride does not play the role of a chemical promoter in the reaction.

The process of the invention may be carried out in the presence of at least one additional catalyst of the metal oxide or sulfate type, such as for example $Ag_2O$, $Cu_2O$, FeO or $FeSO_4$.

The reaction is generally effected under atmospheric pressure, however, it may be carried out under a pressure of up to about 60 bars, for example under a nitrogen or supplemental carbon monoxide pressure, but under these conditions the release of the $R^2R^3R^4CH$ alkane is slowed, which may have a detrimental effect on the yield of the reaction.

As an indication, approximately 20 to 120 ml concentrated sulfuric acid are contacted with 0.1 to 0.5 mole of the alkane to be carbonylated; 0.05 to 0.5 mole of formiate are added and the reaction medium agitated vigorously at a temperature preferably between 10° and 40° C.

The treatment and the purification of the raw reaction product is carried out readily by the conventional methods of the extraction of carboxylic acids. Thus, the raw reaction product may be diluted with ice water, decanted and the aqueous phase extracted for example with carbon tetrachloride. The combined organic phases are then extracted by means of a strong base, such as for example an alkaline hydroxide (sodium or potassium) to form the alkaline salt of the carboxylic acid, which passes into the aqueous phase. The acid is decanted by treating it with a strong acid, such as hydrochloric acid, then extracting the aqueous phase for example by chloroform. The solvent is evaporated from the medium, which contains the carboxylic acid desired.

The following examples illustrate the invention without limiting it. In the examples, percentages are given by weight.

EXAMPLE 1

In a 250 ml reactor, containing 100 ml concentrated sulfuric acid and 0.3 mole methylcyclohexane, 0.2 mole isobutyl formiate is added, the reaction medium is vigorously agitated at 26° C. for 4 h. Subsequently, the mixture is poured into 200 g crushed ice and the aqueous phase extracted with two times 50 ml carbon tetrachloride. The organic phases are treated with 2N sodium hydroxide to Ph 9. The basic aqueous phase is reacidified with 1N hydrochloric acid to pH 1. The acids are extracted with two times 100 ml chloroform. The organic phases obtained are combined and treated in a rotating evaporator to eliminate the solvent. The yield in 1-methylcyclocarboxylic acid is 34.8%.

EXAMPLE 2

The process of Example 1 is repeated, but with the introduction of 50 ml sulfuric acid and the addition of 0.1 mole formic acid. The yield in 1-methylcyclohexylcarboxylic acid is 37.5%.

EXAMPLE 3

The process of Example 1 is repeated, but with the introduction of 50 ml sulfuric acid and is carried out at 20° C. The yield in 1-methylcyclohexylcarboxylic acid is 45.2%.

EXAMPLE 4

The process of Example 1 is repeated, but with the introduction of 50 ml sulfuric acid and the addition of 0.1 mole formic acid and 0.1 g copper oxide and is carried out at 20° C. The yield in 1-methylcyclohexylcarboxylic acid is 67.7%.

EXAMPLE 5

The process of Example 1 is repeated, but with the introduction of 50 ml sulfuric acid and the reaction is carried out at 30° C. The yield in 1-methylcyclohexylcarboxylic acid is 57.5%.

EXAMPLE 6

The process of Example 1 is repeated, but with the introduction of 50 ml sulfuric acid and the reaction is carried out at 40° C. The yield in 1-methylcyclohexylcarboxylic acid is 40%.

EXAMPLE 7

The process of Example 1 is repeated, but with the introduction of 50 ml sulfuric acid and the reaction is carried out at 10° C. The yield in 1-methylcyclohexylcarboxylic acid is 14%.

EXAMPLE 8

The process of Example 1 is repeated, but with the introduction of 50 ml sulfuric acid and the reaction is carried out at 30° C., in the presence of 0.2 mole formic acid per 0.1 mole of isobutyl formiate. The yield in 1-methylcyclohexylcarboxylic acid is 61%.

EXAMPLE 9

The process of Example 1 is repeated, but with the introduction of 50 ml sulfuric acid and the reaction is carried out at 30° C., in the presence of 0.1 g copper oxide. The yield in 1-methylcyclohexylcarboxylic acid is 45%.

EXAMPLE 10

The process of Example 1 is repeated, but with the introduction of 32 ml sulfuric acid and the reaction is carried out at 30° C. The yield in 1-methylcyclohexylcarboxylic acid is 23%.

EXAMPLE 11

The process is carried out as in Example 3, but the alkane introduced is 2,3-dimethylbutane. The yield in 2,2,3-trimethylbutanoic acid is 43.3%.

EXAMPLE 12

The process of Example 11 is repeated, but the reaction is carried out at 30° C. The yield in 2,2,3-trimethylbutanoic acid is 30.7%.

EXAMPLE 13

The process is carried out as in Example 5, but the alkane introduced is decaline. The yield in decalylcarboxylic acid is 40%.

EXAMPLE 14

The process is carried out as in Example 5, but tertiobutylformiate is used at a temperature of 15° C. The yield in 1-methylcyclohexylcarboxylic acid is 30%.

EXAMPLE 15

The process is carried out as in Example 5, but with the introduction of a mixture of 20 ml phosphoric acid and 50 ml sulfuric acid, the temperature of the reaction is 30° C. The yield in 1-methylcyclohexylcarboxylic acid is 30%.

EXAMPLE 16

The process is carried out as in Example 5, but a molar methylcyclohexane/isobutyl formiate equal to 2 is used. The yield in 1-methylcyclohexylcarboxylic acid is 41%.

EXAMPLE 17

The process is carried out as in Example 5, but a molar methylcyclohexane/isobutyl formiate ratio of 1 is used. The yield in 1-methylcyclohexylcarboxylic acid is 43.8%.

EXAMPLE 18

The process is carried out as in Example 5, but 0.6 mole water is introduced. The yield in 1-methylcyclohexylcarboxylic acid is 10%.

EXAMPLE 19

The process is carried out as in Example 1, but under a pressure of 26 bars of carbon monoxide. The yield in 1-methylcyclohexylcarboxylic acid is 16%.

EXAMPLE 20

The process is carried out as in Example 5, but the alkane introduced is adamantane. The yield in adamantylcarboxylic acid is 90%.

EXAMPLE 21

The process is carried out as in Example 5, but the alkane introduced is adamantane and 0.15 mole water is introduced. The yield in adamantylcarboxylic acid is 80%.

We claim:

1. A process for the preparation of a carboxylic acid represented by the Formula (I):

$$R^1\text{—COOH} \quad (I)$$

wherein $R^1$ represents a tertiary branched alkyl radical or a cycloalkyl radical with at least one ring, and which is optionally substituted by at least one alkyl radical, and further where the carbon in alpha of the carbonyl group is a tertiary carbon atom, comprising reacting a branched or cyclic alkane of Formula (II):

$$R^1H \quad (II)$$

in which $R^1$ is a branched alkyl radical or cycloalkyl radical with at least one ring and which is optionally substituted by at least one alkyl radical, and where the carbon atom in alpha of the hydrogen atom is a tertiary atom or a secondary atom which is capable of being rearranged during the course of the reaction into a tertiary atom, with a formiate of Formula (III):

(III)

wherein $R^2$, $R^3$ and $R^4$ each independently represent a hydrogen atom or an alkyl radical, with the following three provisos: (i) $R^2$, $R^3$ and $R^4$ do not simultaneously represent a hydrogen atom, (ii) the compound (III) leads in the reaction medium, directly, or after rearrangement, to a stable cation, $R^2R^3R^4C^+$, and (iii) the alkane formed from the cation may be readily eliminated from the reaction medium, in the presence of an acid catalyst.

2. Process according to claim 1, wherein the alkane (II) is selected so as to provide an alkane of Formula (Ia):

wherein:
- $R^5$, $R^6$ and $R^7$ each independently represent an alkyl radical with $C_1$-$C_{10}$; or
- two radicals $R^5$ to $R^7$ are combined to form a $-(CH_2)_n-$, n being an integer from 4 to 11 and the third represents an alkyl radical $C_1$-$C_7$; or
- $R^5$, $R^6$ and $R^7$ and the carbon atom to which each are attached are combined so as to form a cycloalkyl radical with one, two or three rings.

3. Process according to claim 2, characterized in that as the alkane of Formula (II), the following are used: isopentane, 2,3-dimethyl butane, 2-methyl pentane, 2-methyl hexane, methylcyclopentane, 1,4-dimethyl cyclohexane, decahydronaphthlene and adamantane.

4. Process according to one of the claims 1-3, wherein Formula (III) comprises tertisobutyl formiate or isobutyl formiate.

5. Process according to one of the claims 1-3 wherein the acid catalyst comprises at least one liquid inorganic acid which is used in a concentration of at least 80%.

6. Process according to claim 5, wherein the catalyst comprises sulfuric acid in a concentration of at least 95%.

7. Process according to one of the claims 1-3 wherein the molar ratio of alkane (II)/formiate (III) is between 0.5 and 3.

8. Process according to one of the claims 1-3 wherein the reaction is carried out in a solvent medium.

9. Process according to one of claims 1-3 wherein the reaction is carried out a temperature between 0° C. and the reflux temperature of alkane (II) to be carbonylated.

10. Process according to one of claims 1-3 wherein the reaction has a duration of 1 h to 5 h.

11. Process according to one of the claims 1-3 wherein the reaction is carried out in the presence of at least one additional catalyst comprising a metal oxide or sulfate.

12. The process according to claim 8 wherein the reaction is carried out at a temperature between 0° C. and the reflux temperature of the solvent.

13. The process according to claim 6 wherein the reaction is carried out in the presence of at least one additional catalyst comprising a metal oxide or sulfate.

* * * * *